US009037209B2

(12) United States Patent
Scherer et al.

(10) Patent No.: US 9,037,209 B2
(45) Date of Patent: May 19, 2015

(54) BIO-DIAGNOSTIC TESTING SYSTEM AND METHODS

(71) Applicants: CALIFORNIA INSTITUTE OF TECHNOLOGY, Pasadena, CA (US); SANOFI, Paris (FR)

(72) Inventors: Axel Scherer, Barnard, VT (US); Remi Brouard, III, San Francisco, CA (US); Emil P. Kartalov, Los Angeles, CA (US); Jingqing Huang, Pasedena, CA (US)

(73) Assignees: SANOFI, Paris (FR); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 286 days.

(21) Appl. No.: 13/706,668

(22) Filed: Dec. 6, 2012

(65) Prior Publication Data
US 2013/0149714 A1 Jun. 13, 2013

Related U.S. Application Data

(60) Provisional application No. 61/568,008, filed on Dec. 7, 2011.

(51) Int. Cl.
| A61B 5/1455 | (2006.01) |
| A61B 5/1459 | (2006.01) |
| A61B 3/10 | (2006.01) |
| A61B 5/145 | (2006.01) |
| A61B 5/00 | (2006.01) |
| A61B 5/20 | (2006.01) |
| A61B 5/1491 | (2006.01) |
| A61B 5/01 | (2006.01) |

(52) U.S. Cl.
CPC ............... *A61B 5/1459* (2013.01); *A61B 3/10* (2013.01); *A61B 5/1451* (2013.01); *A61B 5/42* (2013.01); *A61B 5/14507* (2013.01); *A61B 5/4337* (2013.01); *A61B 5/20* (2013.01); *A61B 5/418* (2013.01); *A61B 5/1491* (2013.01); *A61B 5/01* (2013.01); *A61B 5/6848* (2013.01); *A61B 5/6866* (2013.01); *A61B 5/6852* (2013.01); *A61B 5/7278* (2013.01); *A61B 5/0002* (2013.01); *A61B 5/14546* (2013.01); *A61B 2560/0219* (2013.01); *A61B 2560/0233* (2013.01)

(58) Field of Classification Search
CPC ............. A61B 5/14507; A61B 5/1451; A61B 5/14546; A61B 5/1455; A61B 5/1459; A61B 5/1491; A61B 5/418; A61B 5/42; A61B 5/6846; A61B 5/6847; A61B 5/6852; A61B 5/6866; A61B 5/6876; G02B 6/29335; G02B 6/29341
See application file for complete search history.

(56) References Cited

U.S. PATENT DOCUMENTS

| 5,513,636 A | 5/1996 | Palti |
| 2002/0092977 A1 | 7/2002 | Lerber et al. |
| 2004/0186359 A1 | 9/2004 | Beaudoin et al. |

(Continued)

OTHER PUBLICATIONS

International Search Report for PCT Application PCT/US2012/068123 filed on Dec. 6, 2012 in the name of California Institute of Technology. Mail date: Mar. 29, 2013.

(Continued)

*Primary Examiner* — Eric Winakur
(74) *Attorney, Agent, or Firm* — Steinfl & Bruno LLP

(57) ABSTRACT

An implantable diagnostic device in accordance with the present disclosure includes a probe assembly that can be implemented in a variety of ways. A few example implementations include: a needle inside which is located a bio-sensor chip (the needle being insertable into a human being); a compact package containing the bio-sensor chip (the compact package configured for placement inside a catheter); or a silicon-based bio-sensor package configured for insertion into a vein.

25 Claims, 5 Drawing Sheets

(56) References Cited

U.S. PATENT DOCUMENTS

2005/0059166 A1    3/2005   Markes
2005/0177069 A1*   8/2005   Takizawa et al. ............ 600/310
2011/0253909 A1    10/2011  Himmelhaus et al.
2011/0306854 A1*  12/2011   Arnold et al. ................ 600/310

OTHER PUBLICATIONS

Written Opinion of the International Searching Authority for PCT Application PCT/US2012/068123 filed on Dec. 6, 2012 in the name of California Institute of Technology. Mail date: Mar. 29, 2013.

* cited by examiner

BIO-DIAGNOSTIC TESTING SYSTEM AND METHODS

CROSS REFERENCE TO RELATED APPLICATIONS

The present application claims priority to U.S. Provisional Application 61/568,008 filed on Dec. 7, 2011, entitled "Intravenous Protein Detector Using Optical Resonators," which is incorporated herein by reference in its entirety.

FIELD

The present teachings relate to diagnostic devices that are configured for making contact with a flowing fluid such as blood, for carrying out diagnostic tests. More specifically, the present disclosure relates to a probe assembly that includes an optical resonator and circuitry for performing bio-diagnostic tests upon flowing fluids.

BACKGROUND

Bio-diagnostic testing, such as blood tests, are typically performed using on-site or off-site large-scale automated instruments geared towards efficient processing of large batches of prepared fluid samples. However, this type of set-up is not very suitable for emergency care treatment requiring fast turnaround in testing or continuous monitoring of fluids. For example, existing large-scale automated instruments are unsuitable for continuous in-vivo protein measurements upon a patient in an intensive care unit.

Furthermore, treatment of serious cardiovascular conditions, such as myocardial infarction or stroke with anticoagulants or antiplatelet drugs requires accurate and rapid feedback from blood chemistry tests performed upon patients. For such situations, as well as for other situations where for example short-lived proteins are to be measured, it is desirable to provide for improved devices and methods of bio-diagnostic testing.

SUMMARY

According to a first aspect of the present disclosure, a bio-diagnostic system includes a probe assembly configured for insertion into an animate object. The probe assembly includes an optical waveguide configured for propagating a light beam; and further includes an optical resonator incorporating a capture agent placed upon a binding site that is exposed to a fluid. The optical resonator is configured to receive at least a portion of the propagated light beam and generate therefrom, a first resonant wavelength when no binding reaction is present at the binding site, and a second resonant wavelength when a binding reaction is present at the first binding site, the binding reaction modifying a refractive index of the optical resonator.

According to a second aspect of the present disclosure, a bio-diagnostic system includes a probe assembly configured for detecting at least one target molecule in a fluid that makes flowing contact with the probe assembly. The probe assembly includes an optical waveguide configured for propagating a light beam, and further includes an optical resonator incorporating a capture agent placed upon a binding site that is exposed to the at least one target molecule. The optical resonator is configured to receive at least a portion of the propagated light beam and generate therefrom, a first resonant wavelength when no binding reaction is present at the binding site, and a second resonant wavelength when a binding reaction is present at the first binding site, the binding reaction modifying a refractive index of the optical resonator.

According to a third aspect of the present disclosure, a method of using a bio-diagnostic system, includes: i) inserting a first probe assembly into at least one of: a) a first conduit that is propagating a fluid containing at least one target molecule, or b) an animate object, the first probe assembly comprising a bio-sensor chip incorporating an optical waveguide and an optical resonator containing a capture agent placed at a binding site in the optical resonator; ii) propagating light through the optical waveguide; iii) coupling at least a portion of the light from the optical waveguide into the optical resonator; iv) generating in the optical resonator, a first resonant wavelength when no binding reaction is present at the binding site; v) generating in the optical resonator, a second resonant wavelength when a refractive index of the optical resonator is modified as a result of a first binding reaction at the binding site, the first binding reaction characterized by the at least one target molecule binding to the capture agent; and vi) deriving information pertaining to the at least one target molecule upon detecting the change from the first resonant wavelength to the second resonant wavelength.

Further aspects of the disclosure are shown in the specification, drawings and claims of the present application.

BRIEF DESCRIPTION OF THE DRAWINGS

The accompanying drawings, which are incorporated into and constitute a part of this specification, illustrate one or more embodiments of the present disclosure and, together with the description of a few example embodiments, serve to explain the principles and implementations of the disclosure. The components in the drawings are not necessarily drawn to scale. Instead, emphasis is placed upon clearly illustrating various principles. Moreover, in the drawings, like reference numerals designate corresponding parts throughout the several views.

DETAILED DESCRIPTION

Figure 1:
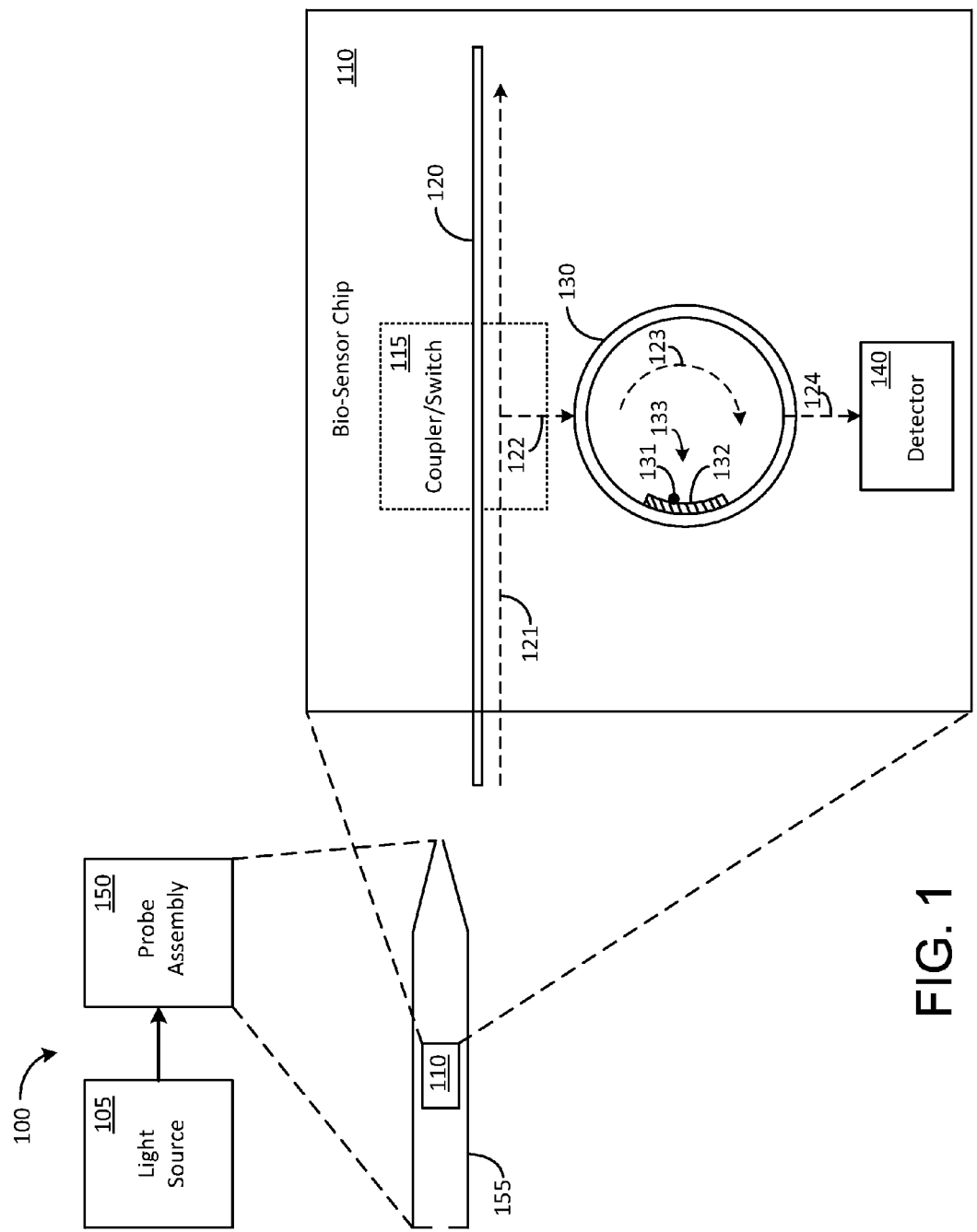
FIG. 1 shows a bio-diagnostic testing system that includes a laser source and a probe assembly in accordance with the present disclosure.

Throughout this description, embodiments and variations are described for the purpose of illustrating uses and implementations of the inventive concept. The illustrative description should be understood as presenting examples of the inventive concept, rather than as limiting the scope of the concept as disclosed herein. Furthermore, the use of certain words and/or phrases should be understood in the context of the description and it should be understood that in some instances alternative words or phrases may be used to refer to substantially similar actions or elements. As one example of such usage, it should be understood that phrases such as a binding site or an immunoassay site generally refer to a location in an optical isolator wherein a binding agent (referred to herein variously as a capture agent or an aptamer) is placed in order to provide a binding mechanism for binding an object of interest (referred to herein variously as molecule, a foreign molecule, a target molecule, or a protein). The use of such words will be understood in a broad sense by persons of ordinary skill in the art and should not be construed as limiting or exclusionary in nature. It will be further understood that the word "in-vivo" is intended to indicate that the probe assembly of the bio-diagnostic system disclosed herein can be implanted inside animate objects. (The phrase "animate object" as used herein in the disclosure represents a wide variety of living objects, such as for example, human beings, animals, mammals, vertebrates, invertebrates, avian species fish, fowl, etc. etc.) However, nothing precludes the bio-diagnostic system from being configured and/or used in various applications outside a living object. For example, the bio-diagnostic system in accordance with the disclosure can be used for carrying out tests (such as an assay test using a hand-held apparatus) for purposes of analyzing a flowing fluid. In some implementations that may not be necessarily viewed as in-vivo applications, the probe assembly described herein may be located in one or more fluid carrying tubes (an intravenous (IV) tube, for example) connected to a living entity, such as a human patient.

In general, when used for in-vivo applications, the bio-diagnostic system in accordance with the disclosure can be used to detect and/or to measure analytes present in various kinds of fluids; and in various locations inside an animate object. Some non-limiting examples of the various kinds of fluids include: blood, lymphatic fluid, cerebrospinal fluid, urine, saliva, vaginal fluid, gall, digestive fluids, ocular fluids etc. Some non-limiting examples of the various locations inside an animate object include locations inside various organs and tissues, as well as locations on the outside of various organs and tissues (such as, for example, on the outside surface of a vein, or in the vicinity of lung tissue).

The various embodiments described herein are generally directed at a bio-diagnostic system that includes a probe assembly. The probe assembly may be implemented in a variety of ways. A few example implementations include: a needle inside which is located a bio-sensor chip (the needle being insertable into a human being); a compact package containing the bio-sensor chip (the compact package configured for placement inside a catheter or for in-vivo applications); or a silicon-based bio-sensor package configured for insertion into a vein.

More particularly, a diagnostic system in accordance with the present disclosure includes a probe assembly that incorporates a bio-sensor chip fabricated in silicon. The probe assembly can be used for label-free identification of binding reactions in real-time, in in-vivo environments, as well as in various other environments wherein testing can be carried out on flowing fluids. The testing procedures and devices disclosed herein provide significantly higher sensitivity than those obtained using conventional immunoassay and ELISA techniques. These, and other, features of the bio-diagnostic system will be described below in further detail using the various figures.

Attention is first drawn to FIG. 1, which shows a bio-diagnostic system 100 that includes a light source 105 and a probe assembly 150 in accordance with the present disclosure. Light source 105 can be implemented via a variety of commercially available devices. For example, light source 105 can be a near-infrared communications laser system that generates a laser beam at near-infrared wavelengths. The laser beam can be coupled into probe assembly 150 using an optical fiber or other suitable communication media.

Probe assembly 150 can be implemented in various ways, some of which will be described below in more detail using other figures.

In the example bio-diagnostic system 100 shown in FIG. 1, probe assembly 150 is depicted as a needle 155 housing a bio-sensor chip 110 inside. The dimensions of needle 155 can vary depending on various operating environments. In one example implementation, needle 155 has a sub-mm diameter. Needle 155 can be composed of any material that is ordinarily used for hypodermic applications, such as, for example, stainless steel, or can be composed of certain non-traditional materials. As for non-traditional materials, in one embodiment described below in more detail, needle 155 is composed of a silicon material.

It should be understood that needle 155 can propagate a fluid in either direction depending for example, on the nature of use of a piston mechanism (not shown). Specifically, fluid flow in a first direction can correspond to using needle 155 for drawing blood, for example, while fluid flow in the opposite direction can correspond to injecting a medication into a patient, for example. The piston mechanism used in hypodermic syringes is known to persons of ordinary skill in the art and will not be described herein so as to avoid distracting from certain primary aspects of the disclosure.

Irrespective of the direction of fluid flow, bio-sensor chip 110 is arranged so as to be exposed to flowing fluid in order to allow one or molecules to make contact and undergo a binding reaction in an optical resonator. The binding reaction is detected via a change in resonant wavelength in the optical resonator and interpreted accordingly so as to derive information about a molecular content of the flowing fluid. For example, when needle 155 is inserted into a vein of a human being, bio-sensor chip 110 can be used to quantify intravenous thrombin levels in blood. Using probe assembly 150, and more particularly, needle 155, in this manner provides thrombin related information on "fresh blood" that is circulating in a vein rather than on extracted blood (as in prior art in-vitro testing), thereby providing measurements that accurately reflect clinically relevant thrombin levels. It will be understood that probe assembly 150 (in the various embodiments described herein) can be implanted/inserted into various types of fluid-carrying elements, both natural as well as man-made. A few examples of natural fluid-carrying elements include: a vein, an artery, a lymphatic vessel, a tissue, or an organ such as the brain for example, while a few examples of man-made fluid-carrying elements include: a catheter and an IV tube.

Furthermore, in contrast to the measuring techniques and devices described herein, prior art techniques that incorporate electrical measurements would be difficult to adapt for a "back end" detection process because ion and cholesterol concentrations in blood would interfere with the electrical measurements.

Another advantage of the measuring techniques and devices described herein arises from the fact that the measurement devices provide high temperature durability; a significant shelf life without deterioration; and permit measurements without swapping out devices for a significant period of time. Such features are advantageous for use in various measurement environments such as an operating theater, or an extensive care ward of a hospital.

Needle 155 houses a bio-sensor chip 110 that contains an optical waveguide 120 for propagating a laser beam injected into probe assembly 150 when light source 105 is a coherent light source. In contrast to probe assembly 150, which is designed for various in-vivo environments, light source 105 is typically located outside an animal or human being. However, in certain embodiments, light source 105 may be configured for insertion into the animal or human being, either as an integrated package that contains both light source 105 as well as probe assembly 150; or as a separate first package containing light source 105, with the first package coupled to a second in-vivo package containing bio-sensor chip 110.

A portion of the coherent light beam injected by light source 105 into optical waveguide 120 is diverted from the main light beam path 121 as an auxiliary light beam that is coupled into optical resonator 130 via an auxiliary light beam path 122. The diversion may be carried out in a variety of ways. For example, in a first implementation, coupler/switch 115 is a coupler that taps into the main light beam path 121 to access a portion of the light beam. In a second implementation, coupler/switch 115 is an optical switch that diverts all or a portion of the coherent light beam from main light beam path 121 into auxiliary light beam path 122. Optical couplers and optical switches are known in the art, and will not be elaborated upon herein so as to avoid detracting from the primary focus of the present disclosure.

The coherent light beam propagated via auxiliary light beam path 122 is coupled into optical resonator 130 where the beam is circulated (as indicated by arrow 123) in order to generate a resonant wavelength. Optical resonator 130 is shown in FIG. 1 as a circular resonator, but it should be understood that optical resonator 130 may be implemented in a variety of ways, including resonators having a non-circular structure.

Auxiliary light beam path 122 that is coupled into optical resonator 130 is directed into an optical resonant cavity, for example, a "whispering gallery" structure (not shown) that is known in the prior art. In general, when broad spectrum light is introduced into an optical resonant cavity, only specific wavelengths, referred to herein as resonant wavelengths, are reinforced inside the optical resonant cavity as a result of constructive interference. The resonant wavelengths are determined on the basis of a length of an optical path in a waveguide structure of the optical resonant cavity (for example, a length of the propagation path in a whispering gallery). More specifically, resonant wavelengths are determined on the basis of optical path lengths configured in accordance to integer multiples of the respective half-wavelengths of the resonant wavelengths.

In the present disclosure, optical resonator 130 provides for at least two resonant wavelengths. The first resonant wavelength is determined by a first optical characteristic of optical resonator 130, particularly, in terms of a first optical signal path length, an absorption parameter, and/or a first refractive index of the optical signal path length. One or more of these parameters are defined in part by a binding site 133. Binding site 133, which is located upon an internal surface of the optical resonant cavity of optical resonator 130, contains a capture agent 132 (an aptamer, for example). Capture agent 132 is selectively located on the internal surface in a manner that facilitates a foreign molecule 131 (alternatively referred to herein as a "target" molecule) from binding to capture agent 132. The foreign molecule 131 may be a target molecule, such as a thrombin molecule, flowing in a blood stream of a human being. Further details pertaining to this topic will be provided below.

The first resonant wavelength is defined when no foreign molecule 131 is bound to capture agent 132 present at binding site 133.

In contrast, a second resonant wavelength is defined when a foreign molecule 131 is present at binding site 133. The presence of the foreign molecule 131 at binding site 133 modifies the refractive index of the first optical signal path, thereby changing the first resonant wavelength to the second resonant wavelength.

The shift from the first resonant wavelength to the second resonant wavelength provides an indication that foreign molecule 131 is present at binding site 133. In other words, bio-sensor chip 110 uses the resonant wavelength shift for detecting an occurrence of a bio-molecular binding. Such a wavelength-oriented detection process not only provides high detection sensitivity in probe assembly 150 but also provides additional advantages. For example, probe assembly 150 in accordance with the disclosure can be used for re-usable, label-free bio-molecular detection in real time or near-real time (at millisecond intervals, for example).

Bio-sensor chip 110 further includes a detector 140, which, in contrast to expensive, complex and bulky prior art detection devices, can be fabricated on silicon inside the same package containing optical resonator 130, thereby providing various advantages such as compact size, low cost, and high detection sensitivity.

Detector 140 is basically an optical-to-electrical converter (O/E converter) that accepts light provided out of optical resonator 130, and generates an electrical signal, say in the form of a detector current. More specifically, detector 140 generates a first electrical signal (say, a first detector current) in response to light provided by optical resonator 130 at the first resonant wavelength, and generates a second electrical signal (say, a second detector current) in response to light provided by optical resonator 130 at the second resonant wavelength.

Figure 2:
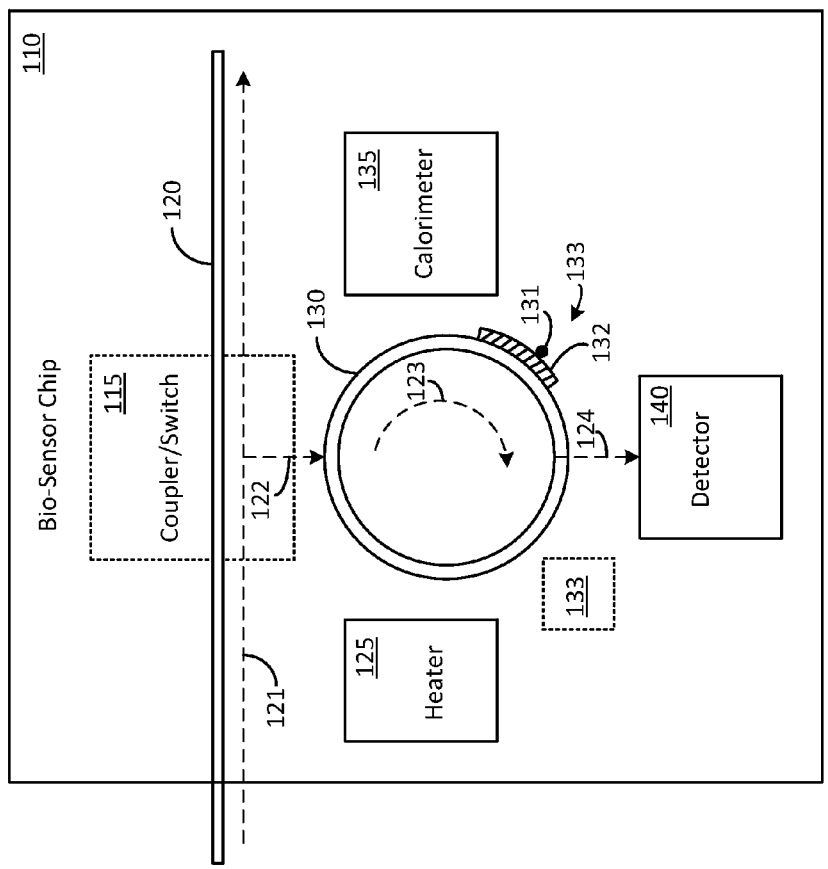
FIG. 2 shows an alternative embodiment of a bio-sensor chip shown as a part of the probe assembly in FIG. 1.

In addition to incorporating detector 140, in some implementations, bio-sensor chip 110 incorporates a heater 125 and a calorimeter 135. One such version of bio-sensor chip 110 is shown in FIG. 2. It should be understood that in variations of the version illustrated in FIG. 2, one or more elements, such as heater 125, calorimeter 135 and detector 140 for example, can be excluded from bio-sensor chip 110.

Furthermore, optical resonator 130 can be fabricated in a variety of ways. For example (as is shown in FIG. 2), binding site 133 and capture agent 132 can be located upon an external surface of optical resonator 130 rather than on an internal surface (as shown in FIG. 1). In general it should be understood that binding site 133 and capture agent 132 can be located at any other suitable location with reference to optical resonator 130 as long as this location permits optical resonator 130 to undergo a shift from a first resonant wavelength to a second resonant wavelength when a foreign molecule 131 binds to binding site 133. Such locations include one that is shown in FIG. 2 in dashed-line outline, where binding site 133 and capture agent 132 are not in direct contact with optical resonator 130).

Heater 125 is used to heat optical resonator 130, and more particularly in some cases, at least a portion of optical resonator 130 that houses binding site 133. Heating can be carried out for a variety of reasons. For example, heating can be carried out to detect and record a thermal response of foreign molecule 131 when bound to capture agent 132 at binding site 133, and/or to release foreign molecule 131 from capture agent 132 in order to prepare binding site 133 to accommodate another foreign molecule 131 (of the same type, or a different type) as part of a subsequent diagnostic test.

When used for recording a thermal response, detector 140 provides data via various electrical signals (for example, detector currents) that correspond to various resonant wavelengths. The data may be mapped as a graph of a slope of resonance shift versus time. Since the slope increases with say, an antigen concentration, a standard curve can be compiled to calibrate the antigen concentration over time. The standard curve may then be used to identify unknown concentration values based on one or more electrical signals generated in detector 140.

As pointed out above, detector 140 provides various advantages for example, in terms of lower cost in comparison to prior art externally located measurement equipment, and in terms of increased efficiency and performance as a result of integration into an implantable package in proximity to optical resonator 130.

Calorimeter 135 can be used to measure the temperature of optical resonator 130, or more particularly in some cases, of binding site 133, when detector 140 is used to generate the various signals thereby facilitating mapping of the graph described above. Integrating calorimeter 135 inside bio-sensor chip 110 provides various advantages, for example, in terms of lower cost in comparison to prior art externally located calorimeters, and in terms of increased efficiency and performance as a result of being located in proximity to optical resonator 130. However, it will be understood that in some implementations, calorimeter 135 may not be included in its entirety inside bio-sensor chip 110 but may instead be located external to bio-sensor chip 110. For example, a temperature sensor may be located inside bio-sensor chip 110 and a read-out unit may be located external to bio-sensor chip 110. (It may also be pertinent to point out that FIGS. 1 and 2 do not show connectivity and access elements, such as metal tracks, wires, pins, and connectors, so as to avoid obfuscating the main focus of the disclosure).

In general, in accordance with the disclosure, bio-sensor chip 110 can be fabricated and packaged in a variety of ways in accordance with a variety of applications. In a first example application, optical waveguide 120 is fabricated as an optical fiber (with a suitable coupler/switch 115 placed in-line with the optical fiber). In a second example application, optical waveguide 120 is fabricated as a groove, a trench, or a rail fabricated upon say, a semiconductor layer inside an integrated circuit (IC). Optical resonator 130 can be fabricated as a groove, a trench, a double-ring, or a protrusion upon the semiconductor layer inside the IC. When optical resonator 130 is fabricated in this manner, binding site 133 and capture agent 132 can be located upon any suitable surface of the groove, trench, double-ring, or protrusion. Suitable surfaces include one or more internal, external, exposed, or enclosed surfaces.

Figure 3:
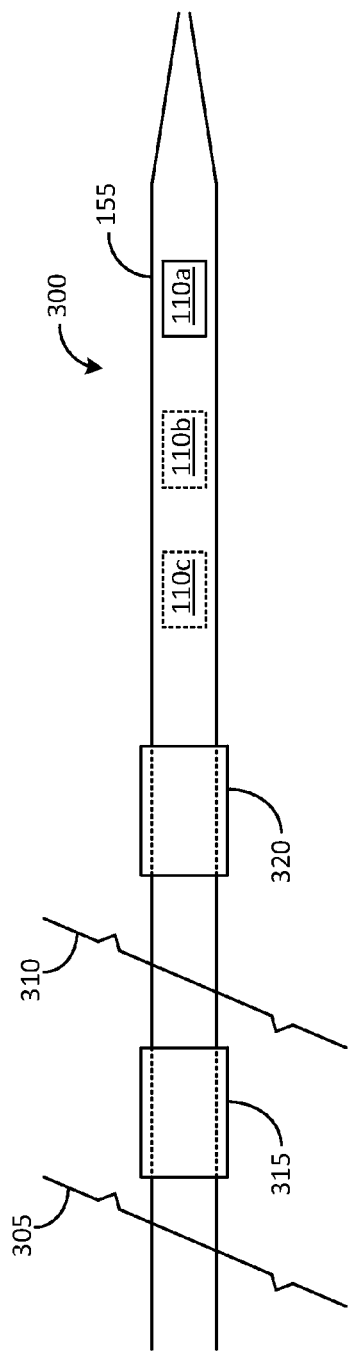
FIG. 3 shows a first example embodiment of a probe assembly in accordance with the present disclosure.

Attention is now drawn to FIG. 3, which shows a first example embodiment of a probe assembly 300 in accordance with the present disclosure. This embodiment expands on certain aspects of needle 155 described above by adding certain other elements to needle 155 that allow probe assembly 300 adapted for sub-cutaneous insertion. Specifically, probe assembly 300 includes a subcutaneous cuff 305 and a peritoneal cuff 320. When probe assembly is inserted into a living object, such as a human patient, subcutaneous cuff 305 is positioned below outer skin layer 305, while peritoneal cuff 320 is positioned in a peritoneal cavity located inside the living object.

Needle 155 may not only house a single bio-sensor chip 110a, but, in certain applications, may include additional bio-sensor chips (such as bio-sensor chips 110b and 110c shown in dashed line outlines).

Figure 4:
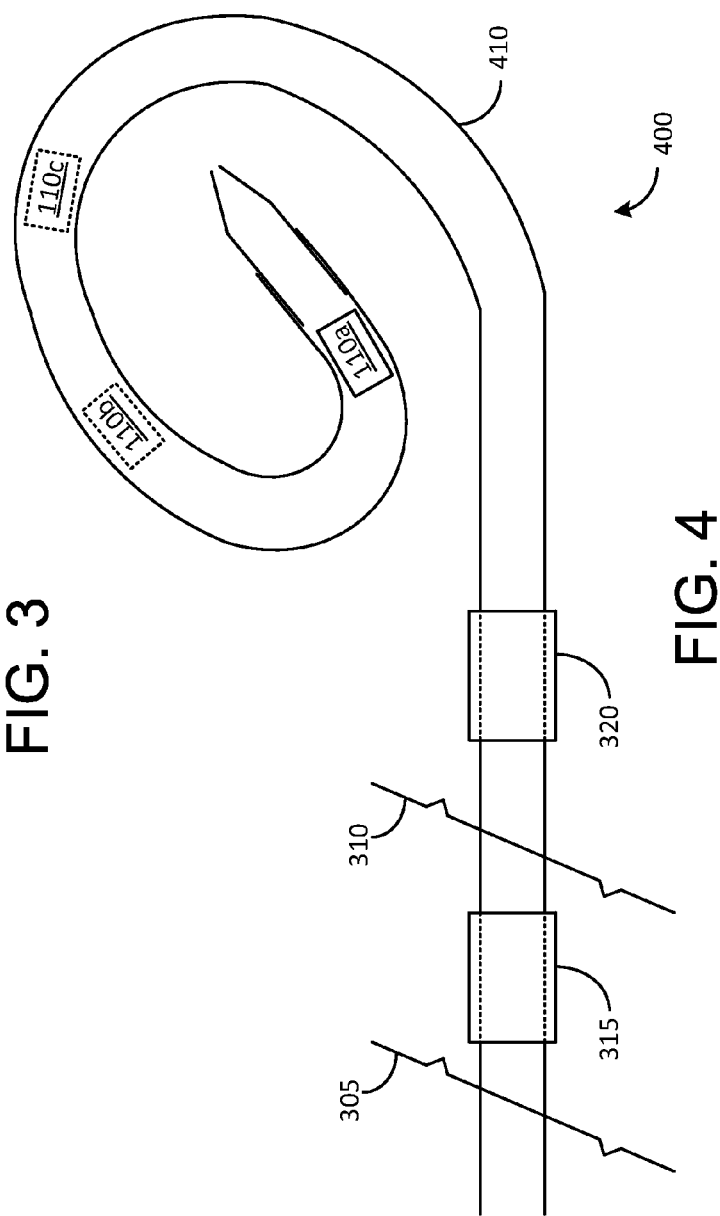
FIG. 4 shows a second example embodiment of a probe assembly in accordance with the present disclosure.

FIG. 4 shows a second example embodiment of a probe assembly 400 in accordance with the present disclosure. In contrast to the needle embodiment described above using FIG. 3, probe assembly 400 is implemented in the form of a catheter 410 that includes subcutaneous cuff 305 and peritoneal cuff 320. Catheter 410 allows flexible sub-cutaneous insertion of one or more bio-sensor chips (110a, 110b and 110c) that may be more suitable for certain types of applications, such as for example, for testing fluids flowing through conduits (an IV tube for example). Furthermore, rather than being limited to "within blood" detection, probe assembly 400 can be used for testing various types of fluids including dialysates, water, bicarbonate, and/or in a high glucose concentration inducing osmotic exchange.

Figure 5:
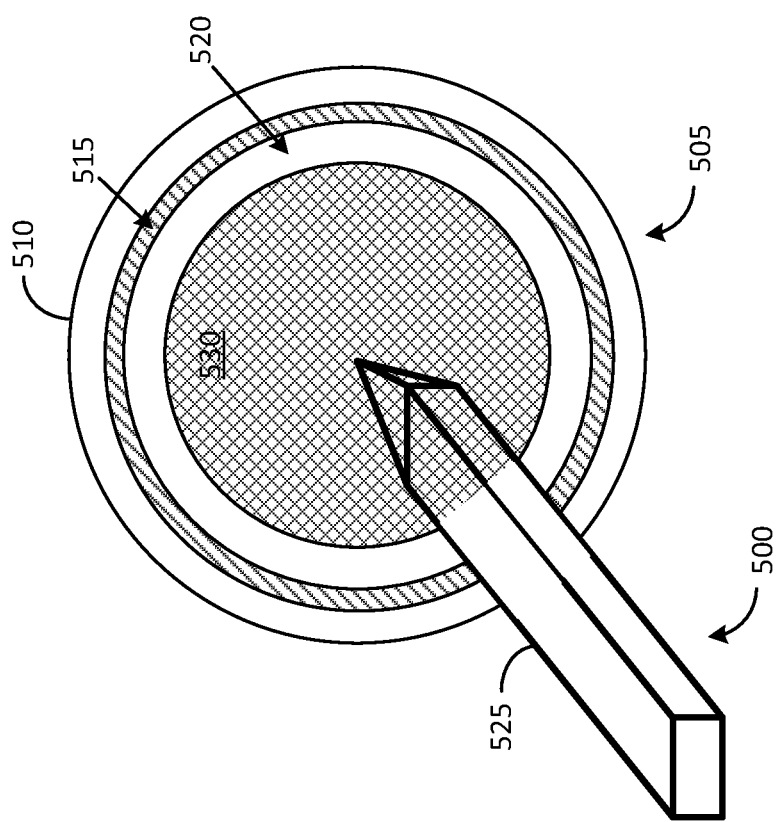
FIG. 5 shows a third example embodiment of a probe assembly in accordance with the present disclosure.

FIG. 5 shows a third example embodiment of a probe assembly 500 in accordance with the present disclosure. In this embodiment, probe assembly 525 is a silicon-based biosensor assembly that is insertable into a living object. In other words, probe assembly 525 can be used in place of needle 155 described above with reference to FIG. 3.

Probe assembly 525 is fabricated using silicon fabrication techniques (for example CMOS-based IC fabrication techniques), and includes an optical resonator and additional elements (such as a detector, heater, and/or calorimeter) that are all fabricated using IC fabrication technology. Probe assembly 525 is inserted into a vein 505 such that a sharp end of probe assembly 525 penetrates through the outer layer (adventitia 510), the middle layer (media 515), and inner layer (intima 520) before entering the blood-carrying area of vein 505, whereby blood 530 flows over one or more optical resonators (not shown) in probe assembly 525. The flowing blood may carry certain target molecules, for example, thrombin, which binds to the capture agent provided in the one or more optical resonators. In this case, the capture agent can be a suitable aptamer. Multiple measurements may be carried out upon the flowing blood 530 in order to obtain average measurement values for example.

In such an arrangement, wherein probe assembly 525 is inserted into vein 505, the flowing blood (as well as the use of heater 125) continuously cleanses contact surfaces of probe assembly 525, thereby overcoming certain prior art issues wherein the contact surfaces of the monitoring equipment cause thrombin levels to change thereby corrupting measurements. The measurements performed in accordance with the present disclosure can be used for obtaining average readings of protein by carrying out multiple measurements over time without withdrawing probe assembly 525 from vein 505.

In one example implementation, probe assembly 525 is provided as a silicon shaft that is 100-500 micrometers wide and several millimeters long. Miniature waveguides and optical resonators are defined upon this silicon shaft. The capture agent can be coated on to the silicon shaft at the binding sites. All or some of the optical elements of probe assembly 525 can be lithographically arranged in the silicon shaft through fabrication processes such as optical or electron beam printing. Furthermore, probe assembly 525 may contain multiple optical resonators and detectors configured for detecting multiple analytes that may or may not be identical to one another.

Figure 6:
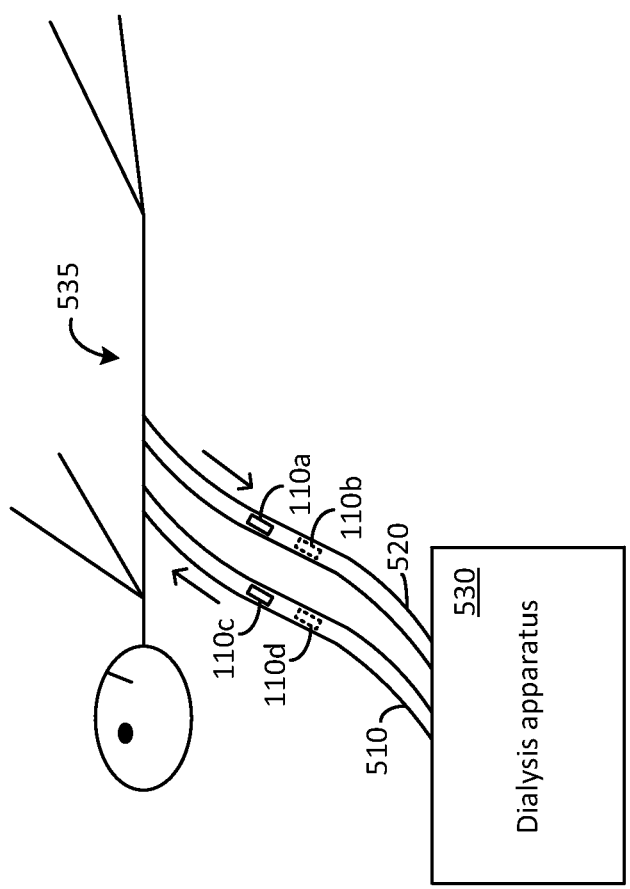
FIG. 6 shows an example bio-diagnostic testing application in accordance with the present disclosure.

FIG. 6 shows an example bio-diagnostic testing application in accordance with the present disclosure. More particularly, this example testing application is part of a dialysis procedure wherein a patient 535 is hooked to a dialysis apparatus 530 via a pair of tubes. The first tube is a catheter 520 that transports blood from patient 535 to dialysis apparatus 530 (as indicated by the arrow) where the blood is processed before being pumped back to patient 535 via a second tube indicted as catheter 510. One or both of catheters 510 and 520 may include one or more bio-sensor chips. Furthermore, one or both of catheters 510 and 520 can be inserted into a peritoneal cavity (for example, a rectouterine pouch or douglas pouch). The inserted catheters 510 and 520, which can be cannulated through the skin of patient 535, can be left in place for various periods of time, including extended periods, such as several hours, a day, a month, a year, or longer.

Bio-sensor chip 110a (and any optional additional bio-sensor chips such as bio-sensor chip 110b) is used to obtain data pertaining to one or more target molecules (thrombin, for example) as the blood flows from patient 535 to dialysis apparatus 530. Similarly, bio-sensor chip 110c (and any optional additional bio-sensor chips such as bio-sensor chip 110d) is used to obtain data pertaining to one or more target molecules as the blood flows from dialysis apparatus 530 back to patient 535. The data so obtained can be used for example to address dialysis efficiency and to monitor patient blood quality as a function of time. In one example bio-diagnostic test, the amount of urea in the blood can be measured before and after processing in the dialysis apparatus 530 by using data obtained from the various bio-sensor chips.

As can be understood, the measurements described herein that can be carried out upon various short-lived molecules (such as proteins in blood) can be very valuable in the monitoring of patient 535 during administration of medicine, or during and after, various kinds of medical procedures. The measurements can be carried out without time delays (as in prior art techniques) and the label-free in-vivo measurements avoid contamination of blood samples and also allow integration of the bio-diagnostic system into standard medical procedures such as dialysis and intravenous (IV) operations.

In conclusion, a bio-diagnostic testing system in accordance with the present disclosure provides various benefits such as various packaging formats, low cost manufacturing, low cost use, in-vivo testing, and improved measurement accuracy and convenience. The various packaging formats include a needle, a catheter, and a silicon-based bio-sensor package. Since each of these packages can be coated with silicone, sterilization of these devices can be carried out conveniently. Furthermore, the catheter packaging accommodates a variety of applications such as dialysis operations, peritoneal operations, and central venous cauterization operations.

When bio-diagnostic testing system 100 is configured for purposes of implanting into an animate object (human being, animal etc.), some elements can be selectively included inside an implantable bio-sensor chip 110 while other elements that operate interactively with bio-sensor chip 110 can be fabricated for use outside the animate object. Furthermore, it will be understood that several elements in addition to those described above, can be incorporated into various embodiments of bio-diagnostic testing system 100.

In one such example embodiment, bio-diagnostic testing system 100 can incorporate a wireless power supply system using various elements in addition to the elements described above using the various figures. In such a wireless power system, a transmitter coil located outside an animate object can be used to transmit power to a receiver coil implanted inside the animate object. The receiver coil can be integrated inside bio-sensor chip 110, or can be a separate element that is placed at a location that is different than that of bio-sensor chip 110. For example, the receiver coil can be placed under the skin of the animate object with suitable wiring connections to bio-sensor chip 110 located elsewhere (inside a vein, artery, or catheter, for example). The power provided to bio-sensor chip 110 can be used for directly powering various elements inside bio-sensor chip 110 (such as detector 140), or can be used for indirect powering by charging a rechargeable battery, which in turn provides power to various elements inside bio-sensor chip 110.

In another example embodiment, bio-sensor chip 110 can incorporate a wired power system. In such a wired power system, a power source located outside the animate object uses wires to provide power to bio-sensor chip 110. The wires may be placed inside a dedicated catheter that is dedicated solely for the purposes of providing power, or in a multi-function catheter that accommodates multiple functionalities. For example, a multi-function catheter can carry fluids while simultaneously housing one or more wires that provide power to bio-sensor chip 110. The wires can provide power to a bio-sensor chip 110 located inside the animate object and/or a bio-sensor chip 110 located inside the multi-function catheter itself (as shown in FIG. 4).

In yet another example embodiment, bio-diagnostic testing system 100 can incorporate a wireless communication system for transferring data between bio-sensor chip 110 (implanted inside an animate object) and one or more communication units located outside the animate object.

The wireless communication system can incorporate a radio-frequency (RF) transmitter inside bio-sensor chip 110. The RF transmitter wirelessly transmits data, such as data from detector 140, out of the animate object. This data is received by a receiver in a communication unit located outside the animate object.

Bio-sensor chip 100 may also include an RF receiver for receiving signals transmitted from the communication unit located outside the animate object. These signals can include commands, controls, or configuration signals.

All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The examples set forth above are provided to give those of ordinary skill in the art a complete disclosure and description of how to make and use the various embodiments of the disclosure, and are not intended to limit the scope of what the inventors regard as their disclosure. Modifications of the above-described modes for carrying out the disclosure may be used by persons of skill in the relevant arts, and are intended to be within the scope of the following claims.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A bio-diagnostic system comprising:
   a probe assembly configured for insertion into an animate object, the probe assembly comprising:
   an optical waveguide configured for propagating a light beam;
   a circular optical resonator incorporating a capture agent placed upon a binding site that is exposed to a fluid, the circular optical resonator configured to receive at least a portion of the propagated light beam and generate therefrom, a first resonant wavelength when no binding reaction is present at the binding site, and a second resonant wavelength when a binding reaction is present at the binding site, the binding reaction modifying a refractive index of the circular optical resonator;

a heating element configured for heating the binding site; and a calorimeter for measuring a temperature of the binding site.

2. The bio-diagnostic system of claim 1, wherein the probe assembly is at least one of: a) a needle comprising a first bio-sensor chip that includes the optical waveguide, the heating element, the calorimeter and the circular optical resonator, b) a catheter comprising a second bio-sensor chip that includes the optical waveguide, the heating element, the calorimeter and the circular optical resonator, or c) a third bio-sensor chip configured for insertion into the vein, the third bio-sensor chip comprising the optical waveguide, the heating element, the calorimeter and the circular optical resonator.

3. The bio-diagnostic system of claim 2, wherein at least one of the needle or the catheter is a part of an intravenous (IV) apparatus.

4. The bio-diagnostic system of claim 2, wherein the needle has a sub-mm diameter.

5. The bio-diagnostic system of claim 4, wherein the fluid is one of: blood, lymphatic fluid, cerebrospinal fluid, urine, saliva, vaginal fluid, gall, digestive fluid, or ocular fluid.

6. The bio-diagnostic system of claim 4, wherein the probe assembly is configured for detecting an analyte at an in-vivo location, the in-vivo location comprising at least one of: i) a location inside a blood vessel, ii) a location inside a lymphatic vessel, or iii) a location inside tissue.

7. The bio-diagnostic system of claim 6, wherein the analyte is detected in at least one of: 1) blood flowing in one of a vein or an artery, or 2) lymphatic fluid in a lymphatic vessel.

8. The bio-diagnostic system of claim 4, further comprising:

a light source for injecting light at near-infrared wavelength into the optical waveguide.

9. The bio-diagnostic system of claim 8, wherein the light source is a near-infrared communications laser, and further wherein each of the first, the second and the third bio-sensor chips further includes a detector for generating a first electrical output signal upon detection of the first resonant wavelength and a second electrical output signal upon detection of the second resonant wavelength.

10. A bio-diagnostic system comprising:

a probe assembly configured for detecting at least one target molecule in a fluid that makes flowing contact with the probe assembly, the probe assembly comprising:

an optical waveguide configured for propagating a light beam;

a circular optical resonator incorporating a capture agent placed upon a binding site that is exposed to the at least one target molecule, the circular optical resonator configured to receive at least a portion of the propagated light beam and generate therefrom, a first resonant wavelength when no binding reaction is present at the binding site, and a second resonant wavelength when a binding reaction is present at the binding site, the binding reaction modifying a refractive index of the circular optical resonator;

a heating element configured for heating the binding site; and a calorimeter for measuring a temperature of the binding site.

11. The bio-diagnostic system of claim 10, wherein the probe assembly includes at least one of: a) a needle comprising a first bio-sensor chip that includes the optical waveguide, the heating element, the calorimeter and the circular optical resonator, b) a catheter comprising a second bio-sensor chip that includes the optical waveguide, the heating element, the calorimeter and the circular optical resonator, or c) a silicon-based probe assembly configured for insertion into the vein, the silicon-based probe assembly comprising the optical waveguide, the heating element, the calorimeter and the circular optical resonator.

12. The bio-diagnostic system of claim 10, further comprising:

a light source for injecting light at near-infrared wavelength into the optical waveguide.

13. The bio-diagnostic system of claim 12, wherein the at least one molecule is a short-lived molecule present in at least one of: a) blood, or b) a dialysate.

14. The bio-diagnostic system of claim 13, wherein the probe assembly is incorporated into a catheter that is a part of at least one of: a) an intravenous (IV) system, or b) a dialysis apparatus.

15. The bio-diagnostic system of claim 12, wherein the probe assembly is configured as one of: a) a needle, b) a catheter, or c) an object that is insertable onto a tube transporting the fluid.

16. A method of using a bio-diagnostic system, comprising:

inserting a first probe assembly into at least one of: a) a first conduit that is propagating a fluid containing at least one target molecule, or b) an animate object, the first probe assembly comprising a bio-sensor chip incorporating an optical waveguide and a circular optical resonator containing a capture agent placed at a binding site in the circular optical resonator;

heating the binding site;

deriving thermal characteristics of the at least one target molecule;

propagating light through the optical waveguide;

coupling at least a portion of the light from the optical waveguide into the circular optical resonator;

generating in the circular optical resonator, a first resonant wavelength when no binding reaction is present at the binding site;

generating in the circular optical resonator, a second resonant wavelength when a refractive index of the circular optical resonator is modified as a result of a first binding reaction at the binding site, the first binding reaction characterized by the at least one target molecule binding to the capture agent; and deriving information pertaining to the at least one target molecule upon detecting the change from the first resonant wavelength to the second resonant wavelength.

17. The method of claim 16, wherein the first conduit is a first tube of a dialysis apparatus, and further comprising:

inserting a second probe assembly into a second tube of the dialysis apparatus;

deriving information pertaining to another at least one target molecule propagating through the second tube; and analyzing the fluid by using at least one of a) the derived information pertaining to the at least one target molecule, or b) the derived information pertaining to the another at least one target molecule.

18. The method of claim 16, wherein the first probe assembly is incorporated into a catheter, and inserting the first probe assembly into the animate object comprises inserting a portion of the catheter into at least one of: a) a peritoneal cavity of an animal, or b) a rectouterine pouch of the animal.

19. The method of claim 18, further comprising:
retaining the portion of the catheter in the one of the peritoneal cavity or the rectouterine pouch for over a day.

20. The method of claim 19 wherein the portion of the catheter is retained in the one of the peritoneal cavity or the rectouterine pouch for at least one year.

21. The method of claim 16, wherein the first conduit is one of a) a vein propagating blood or b) a tube propagating an intravenous (IV) fluid.

22. The method of claim 21, wherein deriving information pertaining to the at least one target molecule comprises deriving information pertaining to a plurality of different types of target molecules.

23. The method of claim 21, wherein deriving information pertaining to the at least one target molecule comprises information pertaining to only a first type of target molecule.

24. The method of claim 21, further comprising:
heating the binding site to desorb the at least one target molecule from the capture agent and prepare the binding site for a second binding reaction.

25. The method of claim 16, wherein heating the binding site and deriving thermal characteristics comprise heating the binding site over a period of time for deriving thermal characteristics over the period of time.

\* \* \* \* \*